(12) United States Patent
Kolobow et al.

(10) Patent No.: US 7,051,737 B2
(45) Date of Patent: May 30, 2006

(54) MUCUS SHAVING APPARATUS FOR ENDOTRACHEAL TUBES

(75) Inventors: Theodor Kolobow, Rockville, MD (US); Lorenzo Berra, San Giacomo (IT)

(73) Assignee: The United States of America as represented by the Department of Health and Human Sevices, Washington, DC (US)

( * ) Notice: Subject to any disclaimer, the term of this patent is extended or adjusted under 35 U.S.C. 154(b) by 0 days.

(21) Appl. No.: 10/773,570

(22) Filed: Feb. 5, 2004

(65) Prior Publication Data

US 2005/0172971 A1 Aug. 11, 2005

(51) Int. Cl.
*A61M 16/00* (2006.01)

(52) U.S. Cl. .............................. 128/207.14; 128/200.26

(58) Field of Classification Search ........... 128/207.14, 128/200.26, 207.15, 207.16, 911, 912; 604/96.01, 604/101.04
See application file for complete search history.

(56) References Cited

U.S. PATENT DOCUMENTS

| | | | |
|---|---|---|---|
| 4,021,265 A * | 5/1977 | Guenther | ................. 134/22.11 |
| 4,116,201 A | 9/1978 | Shah | |
| 4,607,635 A | 8/1986 | Heyden | |
| 4,762,125 A * | 8/1988 | Leiman et al. | ......... 128/207.15 |
| 5,003,657 A * | 4/1991 | Boiteau et al. | .......... 15/104.33 |
| 5,030,213 A * | 7/1991 | Rumberger et al. | ......... 604/267 |
| 5,364,358 A | 11/1994 | Hewitt et al. | |
| 5,687,714 A | 11/1997 | Kolobow et al. | |
| 5,709,691 A | 1/1998 | Morejon | |
| 5,819,723 A * | 10/1998 | Joseph | ................. 128/207.14 |
| 6,082,361 A | 7/2000 | Morejon | |
| 6,318,368 B1 | 11/2001 | Morejon | |
| 6,494,208 B1 | 12/2002 | Morejon | |
| 6,679,262 B1 | 1/2004 | Morejon | |
| 2003/0145860 A1 | 8/2003 | Johnson | |

\* cited by examiner

*Primary Examiner*—Mital Patel
(74) *Attorney, Agent, or Firm*—Townsend and Townsend and Crew LLP; Guy W. Chambers

(57) ABSTRACT

An endotracheal tube cleaning apparatus 10 which can be periodically inserted into the inside of an endotracheal tube 30 to shave away mucus deposits. In a preferred embodiment, this cleaning apparatus 10 comprises a flexible central tube 12 with an inflatable balloon 40 at its distal end. Affixed to the inflatable balloon are one or more shaving rings 70, each having a squared leading edge 72, to shave away mucus accumulations 60. In operation, the uninflated cleaning apparatus 10 is inserted into the endotracheal tube. The balloon 40 is then inflated by a suitable inflation device, such as a syringe 14, until the balloon's shaving rings are pressed against the inside surface of the endotracheal tube. The cleaning apparatus is then pulled out of the endotracheal tube to shave off mucus deposits.

19 Claims, 2 Drawing Sheets

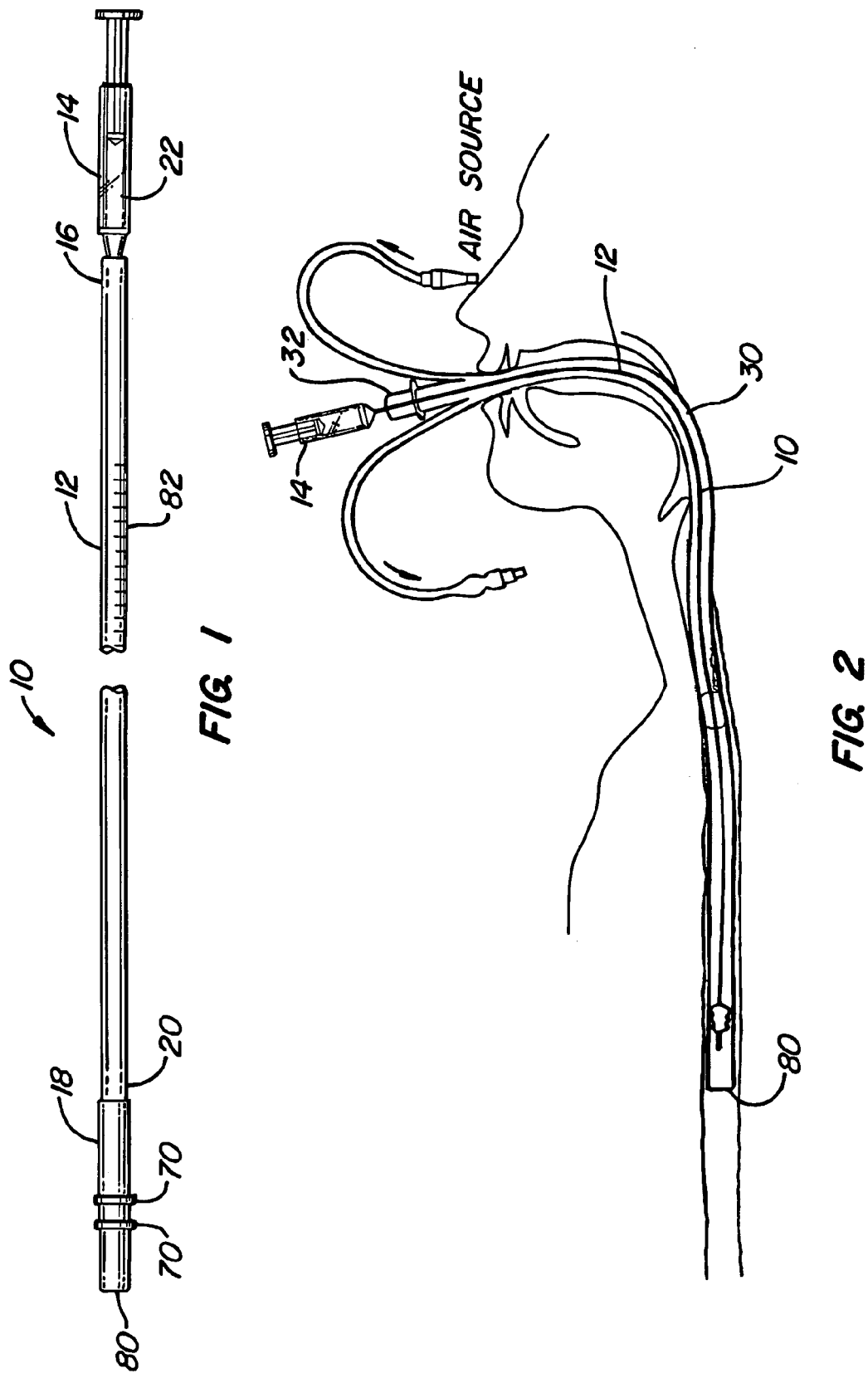

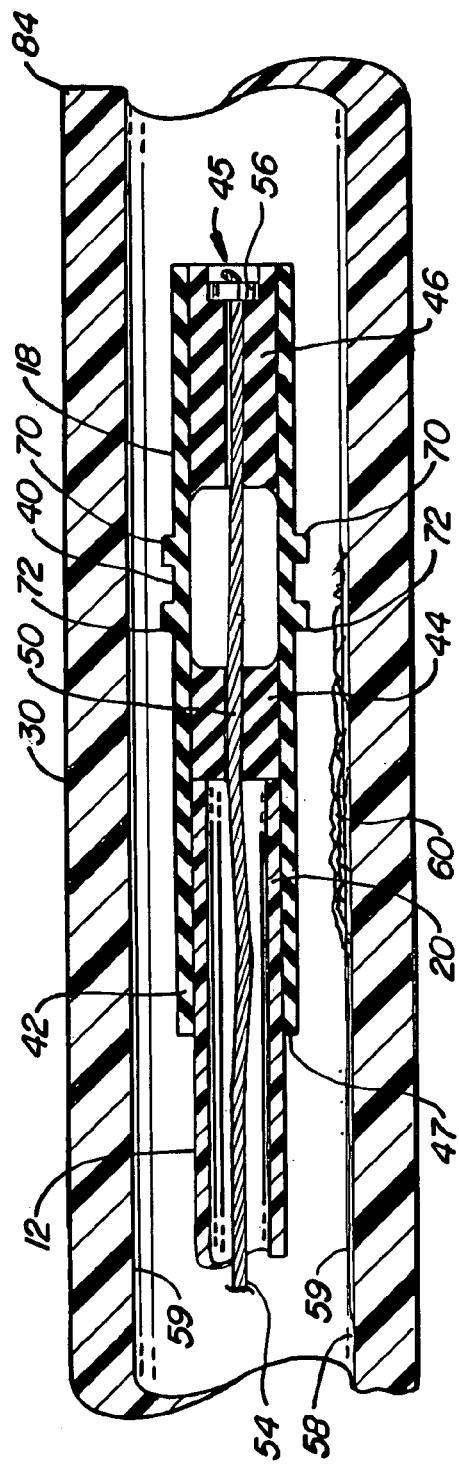
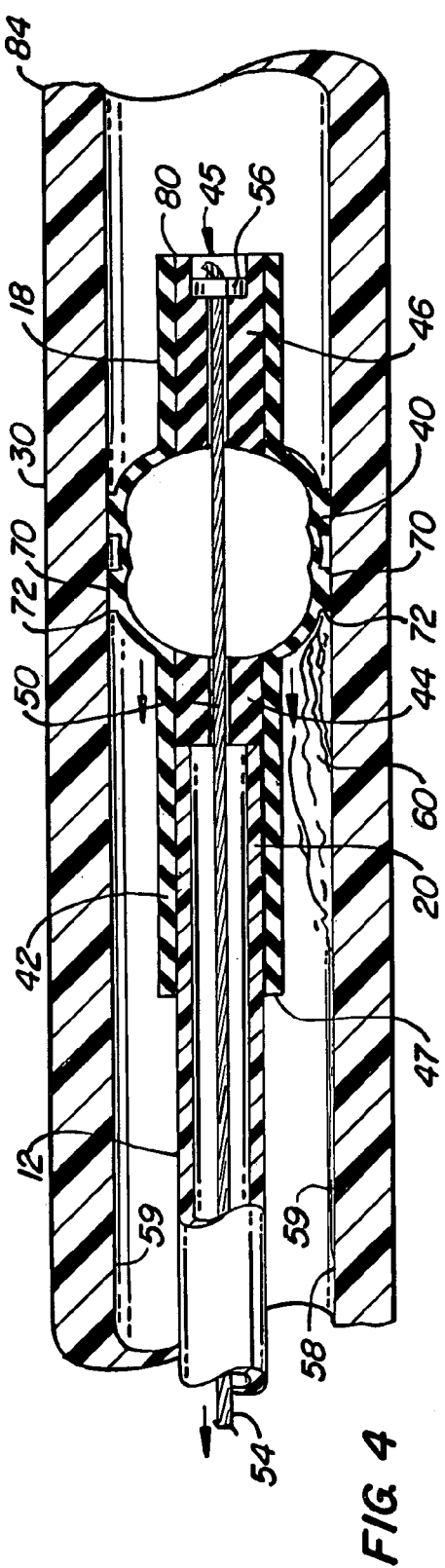
FIG. 3
FIG. 4

MUCUS SHAVING APPARATUS FOR ENDOTRACHEAL TUBES

TECHNICAL FIELD OF THE INVENTION

The present invention relates to the cleaning of medical devices used to assist breathing. More particularly, an inflatable cleaning device is disclosed for shaving mucus accumulations off the inside of endotracheal tubes.

BACKGROUND OF THE INVENTION

Through injury or diseases, human or animal lungs can become too weak to sustain a sufficient flow of oxygen to the body and to remove adequate amounts of expired carbon dioxide. Under these circumstances, it is often necessary to aid the lungs through forms of mechanical assistance, such as mechanical ventilation.

In a common form, mechanical ventilation involves the introduction of an endotracheal tube and, in some cases, a small, open-ended catheter within that tube, into the trachea of a human or animal. The distal ends of the endotracheal tube and/or catheter are positioned to rest at or slightly above the carina of the lungs. A well-humidified oxygen/air mixture is then introduced through the endotracheal tube and/or catheter to provide oxygen to the lungs. In less severe circumstances, the oxygen/air mixture can be supplied through the endotracheal tube and/or catheter using continuous positive airway pressure (CPAP). Where CPAP is used, the patient will use his or her own lung power to exhale the expired gas. In more severe circumstances, it is necessary to use mechanically controlled ventilation with a positive end expiratory pressure (PEEP).

One problem commonly associated with the use of endotracheal tubes is the accumulation of mucus on the inside of the endotracheal tube. In a healthy human, mucus is secreted through glandular action in the trachea/bronchial tree and is progressively transported through the action of cilia along the tracheal airways. Upon nearing the vocal folds, such mucus is either swallowed, coughed up or expectorated.

This mucus transport mechanism is generally not available, though, to a patient intubated with an endotracheal tube. Typically, the endotracheal tube will block the mucus clearing action of the cilia, particularly where an inflatable cuff is used to firmly position the endotracheal tube against the inside wall of the trachea. In such case, instead of being expelled from the lungs and trachea, the mucus will tend to collect on the insides of the endotracheal tube. If such mucus collection is allowed to continue, the internal diameter of the endotracheal tube will become smaller, which makes it more difficult to breathe. Perhaps more seriously, infectious bacteria (e.g., *Staph* and *Pseudomonas* spp.) tend to grow and multiply on the stagnant mucus. The bacteria infected mucus can then aerosolize and deposit into the patient's lungs, leading to ventilator-associated pneumonia.

A number of approaches have been developed to address the mucus accumulation problem for endotracheal tubes. In the most basic approach, the mucus laden endotracheal tube is simply removed from the patient's trachea and replaced with a clean endotracheal tube. Needless to say, removing the mucus laden endotracheal tube is very uncomfortable for patient, particularly since ventilation must be interrupted during the removal process. Moreover, reinsertion of a clean endotracheal tube can lead to tracheal injury, particularly if it is done frequently.

In another common approach, salt water is introduced into the endotracheal tube to dissolve the mucus and a suction catheter is then inserted into the endotracheal tube to try to vacuum up the dissolved mucus deposits. This suctioning approach has a number of drawbacks. First of all, the suctioning process typically takes at least 30 seconds to complete, which can seem like an agonizingly long time for many patients. Secondly, the suction catheter tends to miss a number of the accumulated mucus deposits and thereby leaves them as a breeding ground for infectious bacteria.

A further approach to the mucus accumulation problem is described in the inventor's U.S. Pat. No. 5,687,714. In this approach, droplets of water or saline are entrained in the oxygen/air ventilation mixture to continually dissolve mucus before it has an opportunity to form and a reverse thrust catheter is used to help transport dissolved mucus away from the lungs.

Recently, Dr. Orlando Morejon has received a series of patents for an endotracheal tube cleaning apparatus to remove mucus deposits, including U.S. Pat. Nos. 5,709,691; 6,082,361; 6,318,368, 6,494,208 and 6,679,262. The Morejon cleaning apparatus features an elongate tubular member with an resilient material bladder at its distal end. In operation, Morejon's tubular member is inserted inside of the endotracheal tube at which time Morejon's resilient material bladder is inflated. On the outside of Morejon's resilient material bladder, Morejon forms a generally abrasive surface from a rounded nylon mesh or a plurality of rounded ribs. After the abrasive surface of Morejon's inflated bladder contacts the inner walls of the endotracheal tube, one uses a reciprocating movement to scrub off the mucus deposits. Nonetheless, in the process of Morejon's abrasive scrubbing, bacterially infected mucus particles could aerosolize and work their way back into the patient's lungs, with potentially catastrophic effect.

BRIEF SUMMARY OF THE INVENTION

The present invention provides a endotracheal tube cleaning apparatus which can be periodically inserted into an endotracheal tube to shave away mucus deposits. In a preferred embodiment, this cleaning apparatus comprises a flexible plastic tube with an inflatable balloon at its distal end. Affixed to the inflatable balloon are one or more shaving rings having a squared leading edge to shave away mucus accumulations.

In operation, the uninflated cleaning apparatus of the present invention is inserted into the endotracheal tube until its distal end is properly aligned with or extends slightly beyond the distal end of the endotracheal tube. As soon as the cleaning apparatus is properly aligned, the balloon is inflated by a suitable inflation device, such as a syringe, until the balloon's shaving rings are pressed against the inside of the endotracheal tube. The inflated cleaning apparatus is then pulled out of the endotracheal tube and, in the process, the balloon's shaving rings shave off all the mucus deposits which may have accumulated along the inside of the endotracheal tube.

BRIEF DESCRIPTION OF THE DRAWINGS

FIG. 1 shows a side view of an endotracheal tube cleaning apparatus of the present invention.

FIG. 2 shows a cut-away view of how the endotracheal tube cleaning apparatus of the present invention would appear after being inserted into a patient's endotracheal tube.

FIG. 3 shows a close-up side view of the distal end of an uninflated endotracheal tube cleaning apparatus inside the endotracheal tube.

FIG. 4 shows a close-up side view of the distal end of an inflated endotracheal tube cleaning apparatus inside the endotracheal tube.

DETAILED DESCRIPTION OF THE INVENTION

Referring now to FIG. 1, a preferred form of endotracheal tube cleaning apparatus 10 of the present invention is shown. This cleaning apparatus 10 features a central plastic tube 12 which connects to an inflation device, such as syringe 14, at its proximal end 16, and an inflatable balloon 18 section at its distal end 20. The central tube 12 is preferably formed of a flexible medical plastic and is narrow enough in outside diameter so that it does not unduly impede patient ventilation when it is inserted into the endotracheal tube 30 (see FIG. 2). Nonetheless, it should also be is wide enough in internal diameter to quickly inflate the balloon 40 (see FIG. 4) during the cleaning process. The inventors have found that a 3.0 mm outside diameter, 2.0 mm inside diameter plastic tube made of DuPont HYTREL™ plastic can accomplish these competing objectives, although other sizes and materials of central tubes 12 would also work.

The inflation device at the proximal end of the central tube 12 can take any number of forms, including a simple syringe 14. If a syringe 14 is used, it must have a sufficient internal volume 22 to fully inflate the balloon 40 against the inside of the endotracheal tube 30. A 10 cc syringe has been found to be an effective choice in the inventor's experiments. Instead of a syringe 14, the central tube 12 could be connected to the patient's ventilation equipment (not shown) to use as an inflation device. Nonetheless, as compared with the ventilation equipment, the syringe 14 has the advantage of allowing inflation and deflation of the balloon 40 to be easily responsive to manual control.

The balloon section 18 of the cleaning apparatus 10 is shown in greater detail in FIGS. 3 and 4. In the preferred embodiment, the balloon section 18 features a thin walled balloon tube 42 which is partially fitted over and adhered to the distal end 20 of the central tube 12. This balloon tube 42 should preferably be constructed of a durable, easily inflatable elastomeric material such as silicone rubber. The inventors have had success forming the balloon tube 42 of a 2.0 cm length of General Electric CE-4524 silicone rubber tubing with an outside diameter of 4.5 mm and an inside diameter of 3.5 mm. While the proximal end 47 of the balloon tube 42 needs to be open ended, the distal end 45 of the balloon tube 42 may be either open ended or capped.

Within the balloon tube 42 are a proximal plug 44 and a distal plug 46 which are separated by a sufficient gap to create the balloon 40 itself. These plugs 44, 46 should be formed of an air impermeable, flexible material, such as silicone rubber. In the center of the proximal plug 44, a longitudinal hole should be formed to allow pressurized air to inflate and deflate the balloon 40. As a safety mechanism, a safety wire 54 and anchor 56 can be threaded through the two plugs 44, 46 to retrieve all or part of the balloon section 18 should it happen to become detached from the central tube 12

Assembly of the balloon section 18 of the cleaning apparatus 10 is relatively simple. If the distal end 45 of the balloon tube 42 is capped, the distal plug 46 can first be dropped into the capped distal end of the balloon tube 42. To keep the distal plug 46 in place, a suitable adhesive should be applied to the outside of the plug so that it will adhere to the inside of the balloon tube 42. The proximal plug 44 is then placed in the balloon tube 42 at a sufficient distance from the distal plug 46 to create the balloon 40. Like the distal plug 46, the proximal plug 44 is preferably adhered to the inside of the balloon tube 42 with a suitable adhesive. After the plugs 44, 46 have been inserted into the balloon tube 42, the balloon tube can be adhered to the distal end 20 of the central tube 12. If the distal end 45 of the balloon tube 42 is open ended, assembly of the balloon section 18 can take place in the same sequence or in a reverse sequence. If the distal end 45 of the balloon tube 42 is open, though, it becomes more important to use a strong adhesive and to consider use of a safety mechanism, such as wire 54 and anchor 56, to make sure that the plugs 44, 46 do not disengage from the central tube 12.

When the cleaning apparatus 10 is inserted into the endotracheal tube 30, the inside 58 of the endotracheal tube 30 will likely have mucus accumulations 60. To shave away those mucus accumulations 60, one or more shaving rings 70 are formed on the outside of the balloon 40 portion of the balloon tube 42. These shaving rings 70 are preferably formed from a durable elastomeric polymer. The objective of the shaving rings 70 is to shave away the mucus accumulation layer 60 without scraping into the endotracheal tube 30 itself. The inside 58 of the endotracheal tube 30 may have a bactericidal film, for example, which the cleaning apparatus 10 should leave in place after the mucus accumulation is removed.

The shaving rings 70 may either be formed integrally with the balloon tube 42, such as by injection molding, or adhered to the outside of the balloon tube 42. In one preferred embodiment, two narrow strips (i.e., 1.0 mm wide and 0.5 mm high) of silicone rubber tubing are cemented to the outside of the balloon tube 42 in order to form the shaving rings 70. While the inventors have found that two shaving rings 70 work effectively in the cleaning apparatus 10 of the present invention, those of skill in the art will recognize that other numbers of shaving rings could alternatively be used, such as a single shaving ring 70 or three (or more) shaving rings 70.

To effectively shave away the mucus accumulations 60, the leading edge 72 of at least one of the shaving rings 70 should be essentially squared (i.e., an approximately 90° edge). Preferably, the leading edge 72 of the proximal shaving ring 70 should be squared because it will be doing most of the shaving work. The use of rounded edges would not be effective in accomplishing the shaving processes, which are an important part of the present invention.

The process of using the cleaning apparatus 10 of the present invention to remove mucus accumulations 60 from the inside of endotracheal tubes 30 begins with inserting the distal end 80 of the cleaning apparatus 10 into the endotracheal tube 30. To accomplish this insertion, the endotracheal tube 30 can be disconnected from the ventilation apparatus (not shown) and the cleaning apparatus 10 can then be inserted into the disconnected proximal end 32 of the endotracheal tube 30 (see, FIG. 2). For effective cleaning, the cleaning apparatus 10 should be inserted into the endotracheal tube 30 far enough that the shaving rings 70 of the balloon 40 are approximately coincident with or slightly beyond the distal end 84 of the endotracheal tube. To achieve a desired alignment, measurement markers 82 may advantageously be formed on the outside of the central tube 12 (see, FIG. 1). Alternatively, x-ray detectable markers can be placed at the distal end 84 of the endotracheal tube and in the vicinity of the balloon 40 to assist in using x-rays scanners for proper alignment. One of these x-ray detectable markers could advantageously be a stainless steel anchor 56 which would serve the dual purpose of locating the balloon and acting as an x-ray detectable safety mechanism.

When the cleaning apparatus 10 is properly positioned in the endotracheal tube 30 for cleaning, the syringe 14 or other inflation device is used to inflate the balloon 40 until the shaving rings 70 are pressed flush against the inside surface 58 of the endotracheal tube 30. While the balloon 40 is still fully inflated, the cleaning apparatus 10 should then be steadily withdrawn from the endotracheal tube 30. While the cleaning apparatus 10 is being withdrawn, the leading edge 72 of the shaving ring will shave off the mucus accumulations 60 and pull them back out of the endotracheal tube 30 (see, FIG. 4). After the cleaning apparatus 10 is removed from the endotracheal tube 30, the inside of the endotracheal tube 58 should be effectively free of mucus accumulations. If done correctly, the shaving process should take no more than 3–6 seconds and, thus, not create a significant interruption in the patient's ventilation. For best results, the air ventilated into the patient must be humidified so that the mucus accumulations will remain moist. Cleaning must also be done at regular intervals. The shaving process may become less effective if the mucus accumulations are allowed to dry, either through lack of humidity in the ventilated air or irregular cleanings.

When the cleaning apparatus 10 is removed from the endotracheal tube 30 after the shaving process is finished, it may either be cleaned or discarded. For cleaning, the soiled cleaning apparatus may be immersed in one or more detergent solutions. For example, the soiled cleaning apparatus could be sequentially inserted into three cylinders having a Phisohex™ detergent diluted in water, the first cylinder to dislodge secretions, the second cylinder to rinse and the third cylinder to await reuse. Nonetheless, since the cleaning apparatus 10 of the present invention is relatively simple and inexpensive to manufacture, it would not be unduly burdensome to discard the cleaning apparatus 10 of the present invention after each use to maintain a high degree of sterility.

EXAMPLE I

The cleaning apparatus of the present invention was tested with anesthetized, intubated sheep. The anesthetized sheep were mechanically ventilated for 72–168 hours, with the endotracheal tubes being cleaned approximately every 6 hours using the cleaning apparatus of the present invention. To construct the cleaning apparatus for this experiment, a 3.0 mm outside diameter/2.0 mm inside diameter central plastic tube (Dupont HYTREL™) was connected to a 2.0 cm length of thin silicone rubber balloon tube (General Electric CE-4524, 3.5 mm inside diameter, 4.5 mm outside diameter). Cemented onto the balloon tube were two narrow strips (1.0 mm wide and 0.5 mm high) of the same silicone rubber tubing which were used as the shaving rings. The shaving rings were spaced 1.0 mm apart. Cleaning was accomplished by inflating the balloon using a syringe to tightly fit against the inside wall of the endotracheal tube and shaving the surface of the endotracheal tube with the shaving rings as the inflated cleaning apparatus was removed from the endotracheal tube over a period of 3–6 seconds. Between each use, the cleaning apparatus was immersed in multiple detergent solutions. At the end of the study, the endotracheal tubes were removed from the sheep and sliced open. Upon inspection visually and with a high power scanning electron microscope (×1300), no residual mucus accumulations or bacteria were detected on the insides of the endotracheal tubes.

In the foregoing specification, the invention has been described with reference to specific preferred embodiments and methods. It will, however, be evident to those of skill in the art that various modifications and changes may be made without departing from the broader spirit and scope of the invention as set forth in the appended claims. For example, while air would most commonly be used to inflate the balloon 40, other fluids could alternatively be used, such as water. Further, while the cleaning apparatus of the present invention has been described as a stand alone approach to cleaning mucus accumulations, it can alternatively be used with other approaches. For example, suctioning can first be used to remove large mucus deposits, followed by a shaving of the remaining mucus deposits using the cleaning apparatus of the present invention. Accordingly, the specification and drawings are to be regarded in an illustrative, rather than restrictive, sense; the invention being limited only by the appended claims.

What is claimed is:

1. An endotracheal tube cleaning apparatus comprising:
   an inflation device;
   a balloon having a shaving ring with a squared edge; and,
   a tube connecting said inflation device and said balloon which is capable of transporting fluid from said inflation device to inflate said balloon.

2. The cleaning apparatus of claim 1 wherein said inflation device is a syringe.

3. The cleaning apparatus of claim 1 wherein said tube and said balloon are formed from an elastomer.

4. The cleaning apparatus of claim 1 further comprising a plurality of shaving rings having squared edges.

5. The cleaning apparatus of claim 1 wherein said fluid is air.

6. An endotracheal tube cleaning apparatus comprising:
   an inflation device;
   a balloon having a shaving ring with a squared edge; and,
   a tube connecting said inflation device and said balloon which is capable of transporting fluid from said inflation device to inflate said balloon;
   wherein said balloon is formed as a gap in an elastomeric tube between two plugs within said tube, wherein one of said plugs has a hole in it to allow inflating fluid to enter said balloon.

7. The cleaning apparatus of claim 6 further comprising a wire connecting said plugs.

8. An endotracheal tube cleaning apparatus comprising:
   an inflation device;
   a balloon formed as a gap in a elastomeric tube between two plugs, wherein one of said plugs has a hole in it to allow inflating fluid to enter said balloon;
   a plurality of elastomeric shaving rings affixed to said balloon wherein each of said rings has at least one squared edge; and,
   a tube connecting said inflation device and said balloon which is capable of transporting fluid from said inflation device to inflate said balloon.

9. A process for removing mucus accumulations from the inside walls of an endotracheal tube comprising the steps of:
   selecting a cleaning apparatus capable of shaving said mucus accumulations off the inside walls of said endotracheal tube wherein said apparatus comprises an inflation device, a balloon having a shaving ring with a squared edge, and a tube connecting said inflation device and said balloon;
   inserting said cleaning apparatus into said endotracheal tube;

using said inflation device to inflate the balloon of said cleaning apparatus so that said shaving ring is pressed against the inside wall of said endotracheal tube;

pulling said cleaning apparatus out of said endotracheal tube while said balloon is still inflated so that said shaving ring shaves said mucus accumulations off of the inside walls of said endotracheal tube.

10. The process of claim 9 wherein said inflation device is a syringe.

11. The process of claim 9 wherein said balloon has a plurality of shaving rings with squared edges.

12. The process of claim 9 wherein said balloon is formed from an elastomer.

13. The process of claim 9 wherein said endotracheal tube and said cleaning apparatus have x-ray detectable markers which are used for alignment.

14. A process for removing mucus accumulations from the inside walls of an endotracheal tube comprising the steps of:

selecting a cleaning apparatus capable of shaving said mucus accumulations off the inside walls of said endotracheal tube wherein said apparatus comprises an syringe inflation device, an elastomeric balloon having a plurality of shaving rings with squared edges, a plastic tube connecting said inflation device and said balloon and two plugs adjacent to said elastomeric balloon;

inserting said cleaning apparatus into said endotracheal tube;

using said syringe to inflate the balloon of said cleaning apparatus so that said shaving rings are pressed against the inside wall of said endotracheal tube;

pulling said cleaning apparatus out of said endotracheal tube while said balloon is still inflated so that said shaving rings shave said mucus accumulations off of the inside walls of said endotracheal tube.

15. A process for removing mucus accumulations from the inside walls of an endotracheal tube comprising the steps of:

selecting an endotracheal tube having a bactericidal film on its inside wall;

selecting a cleaning apparatus capable of shaving said mucus accumulations off the inside walls of said endotracheal tube without significantly damaging said bactericidal film wherein said apparatus comprises an inflation device, a balloon having a shaving ring with a squared edge, and a tube connecting said inflation device and said balloon;

inserting said cleaning apparatus into said endotracheal tube;

using said inflation device to inflate the balloon of said cleaning apparatus so that said shaving ring is pressed against the inside wall of said endotracheal tube;

pulling said cleaning apparatus out of said endotracheal tube while said balloon is still inflated so that said shaving ring shaves said mucus accumulations off of the inside walls of said endotracheal tube without significantly damaging said bactericidal film.

16. The process of claim 15 wherein said inflation device is a syringe.

17. The process of claim 15 wherein said balloon has a plurality of shaving rings with squared edges.

18. The process of claim 15 wherein said balloon is formed from an elastomer.

19. A process for removing mucus accumulations from the inside walls of an endotracheal tube comprising the steps of:

selecting an endotracheal tube having a bactericidal film on its inside wall;

selecting a cleaning apparatus capable of shaving said mucus accumulations off the inside walls of said endotracheal tube without significantly damaging said bactericidal film wherein said apparatus comprises an syringe inflation device, an elastomeric balloon having a plurality of shaving rings with squared edges, a plastic tube connecting said inflation device and said balloon and two plugs adjacent to said elastomeric balloon;

inserting said cleaning apparatus into said endotracheal tube;

using said syringe to inflate the balloon of said cleaning apparatus so that said shaving rings are pressed against the inside wall of said endotracheal tube;

pulling said cleaning apparatus out of said endotracheal tube while said balloon is still inflated so that said shaving rings shave said mucus accumulations off of the inside walls of said endotracheal tube without significantly damaging said bactericidal film.

* * * * *